(12) United States Patent  
Williams

(10) Patent No.: US 6,581,899 B2
(45) Date of Patent: Jun. 24, 2003

(54) VALVE FOR USE IN MICROFLUIDIC STRUCTURES

(75) Inventor: Clinton L. Williams, Seattle, WA (US)

(73) Assignee: Micronics, Inc., Redmond, WA (US)

( * ) Notice: Subject to any disclaimer, the term of this patent is extended or adjusted under 35 U.S.C. 154(b) by 45 days.

(21) Appl. No.: 09/887,820

(22) Filed: Jun. 22, 2001

(65) Prior Publication Data

US 2001/0054702 A1 Dec. 27, 2001

Related U.S. Application Data

(60) Provisional application No. 60/213,865, filed on Jun. 23, 2000.

(51) Int. Cl.[7] ................................................. F16K 7/00
(52) U.S. Cl. ............................ 251/7; 257/61; 257/213
(58) Field of Search ...................... 257/7, 4, 5, 213, 257/61, 61.1

(56) References Cited

U.S. PATENT DOCUMENTS

| | | | | |
|---|---|---|---|---|
| 2,660,395 A | * | 11/1953 | Mair et al. ..................... 251/7 |
| 3,572,735 A | * | 3/1971 | Dryer .......................... 251/332 |
| 4,099,700 A | * | 7/1978 | Young ............................ 251/7 |
| 4,341,098 A | * | 7/1982 | Otting ............................ 251/7 |
| 4,895,500 A | | 1/1990 | Hok et al. |
| 4,899,783 A | * | 2/1990 | Yusko et al. .................... 251/7 |
| 5,098,060 A | * | 3/1992 | Mogler et al. .................. 251/7 |
| 5,443,890 A | | 8/1995 | Ohman |
| 5,593,130 A | | 1/1997 | Hansson et al. |
| 5,660,370 A | * | 8/1997 | Webster ...................... 251/61.1 |
| 5,851,004 A | | 12/1998 | Wu et al. |
| 5,863,502 A | | 1/1999 | Southgate et al. |
| 5,932,799 A | | 8/1999 | Moles |
| 5,962,081 A | | 10/1999 | Ohman et al. |
| 5,971,355 A | | 10/1999 | Biegelsen et al. |
| 6,068,751 A | | 5/2000 | Neukermans |
| 6,431,212 B1 | | 8/2002 | Hayenga et al. |

* cited by examiner

Primary Examiner—Ehud Gartenberg
Assistant Examiner—John Bastianelli

(57) ABSTRACT

A valve for use in microfluidic structures. The valve uses a spherical member, such as a ball bearing, to depress an elastomeric member to selectively open and close a microfluidic channel. The valve may be operated manually or by use of an internal force generated to shift the spherical member to its activated position.

16 Claims, 2 Drawing Sheets

VALVE FOR USE IN MICROFLUIDIC STRUCTURES

CROSS-REFERENCE TO RELATED APPLICATIONS

This patent application claims benefit from U.S. Provisional Patent Application Ser. No. 60/213,865, filed Jun. 23, 2000, which application is incorporated herein by reference.

BACKGROUND OF THE INVENTION

1. Field of the Invention

This invention relates generally to microscale devices for performing analytical testing and, in particular, to a valve for use in laminated plastic microfluidic structures.

2. Description of the Prior Art

Microfluidic devices have recently become popular for performing analytical testing. Using tools developed by the semiconductor industry to miniaturize electronics, it has become possible to fabricate intricate fluid systems which can be inexpensively mass produced. Systems have been developed to perform a variety of analytical techniques for the acquisition of information for the medical field.

Microfluidic devices may be constructed in a multi-layer laminated structure where each layer has channels and structures fabricated from a laminate material to form microscale voids or channels where fluids flow. A microscale channel is generally defined as a fluid passage which has at least one internal cross-sectional dimension that is less than 500 $\mu$m and typically between about 0.1 $\mu$m and about 500 $\mu$m. The control and pumping of fluids through these channels is affected by either external pressurized fluid forced into the laminate, or by structures located within the laminate.

Many different types of valves for use in controlling fluids in microscale devices have been developed. U.S. Pat. No. 4,895,500, which issued on Jan. 23, 1990, describes a silicon micromechanical non-reverse valve which consists of a cantilever beam extending over a cavity and integrally formed with the silicon wafer such that the beam can be shifted to control flow within channels of the microfluidic structure.

U.S. Pat. No. 5,443,890, which issued Aug. 22, 1995 to Pharmacia Biosensor AB, describes a sealing device in a microfluidic channel assembly having first and second flat surface members which when pressed against each other define at least part of a microfluidic channel system between them.

U.S. Pat. No. 5,593,130, which issued on Jan. 14, 1997 to Pharmacia Biosensor AB, describes a valve for use in microfluidic structures in which the material fatigue of the flexible valve membrane and the valve seat is minimized by a two-step seat construction and the fact that both the membrane and the seat are constructed from elastic material.

U.S. Pat. No. 5,932,799, which issued Aug. 3, 1999 to YSI Incorporated, teaches a microfluidic analyzer module having a plurality of channel forming laminate layers which are directly bonded together without adhesives, with a valve containing layer directly adhesivelessly bonded over the channel containing layers and a flexible valve member integral with the valve layer to open and close communication between feed and sensor channels of the network.

U.S. Pat. No. 5,962,081, which issued Oct. 5, 1999 to Pharmacia Biotech AB, describes a method for the manufacturer of polymer membrane-containing microstructures such as valves by combining polymer spin deposition methods with semiconductor manufacturing techniques.

U.S. Pat. No. 5,971,355, which issued on Oct. 26, 1999 to Xerox Corporation, describes a valve array system for microdevices based on microelectro mechanical systems (MEMS) technology consisting of a dielectric material forming a laminate which is embedded within multiple laminate layers.

U.S. Pat. No. 6,068,751, which issued on May 30, 2000, describes a microfluidic delivery system using elongated capillaries that are enclosed along one surface by a layer of malleable material which is shifted by a valve having a electrically-powered actuator.

U.S. patent application Ser. No. 09/677,250, filed on Oct. 2, 2000, now U.S. Pat. No. 6,431,212, and assigned to the assignee of the present invention describes a one way check valve for use in laminated plastic microfluidic structures. This valve allows one way flow through microfluidic channels for use in mixing, dilution, particulate suspension and other techniques necessary for flow control in analytical devices.

Several types of valves are commonly used for fluid management in flow systems. Flap valves, ball-in-socket valves, and tapered wedge valves are a few of the valve types existing in the macroscale domain of fluid control. However, in the microscale field, where flow channels are often the size of a human hair (approximately 100 microns in diameter), there are special needs and uses for valves which are unique to microscale systems, especially microfluidic devices incorporating fluids with various concentrations of particulate in suspension. Special challenges involve mixing, dilution, fluidic circuit isolation, and anti-sediment techniques when employing microscale channels within a device. The incorporation of a simple compact valve within microscale devices addresses these potential problems while maintaining high density of fluidic structure within the device.

SUMMARY OF THE INVENTION

It is therefore an object of the present invention to provide an efficient and reliable valve suitable for use in a microfluidic system.

It is a further object of the present invention is to provide a microfluidic valve which can be integrated into a cartridge constructed of multi-layer laminates.

It is a further object of the present invention is to provide an array of microfluidic valves that can be integrated into a cartridge constructed of multilayer laminates.

These and other objects of the present invention will be more readily apparent in the description and drawings that follow.

DETAILED DESCRIPTION OF THE PREFERRED EMBODIMENTS

Figure 1:
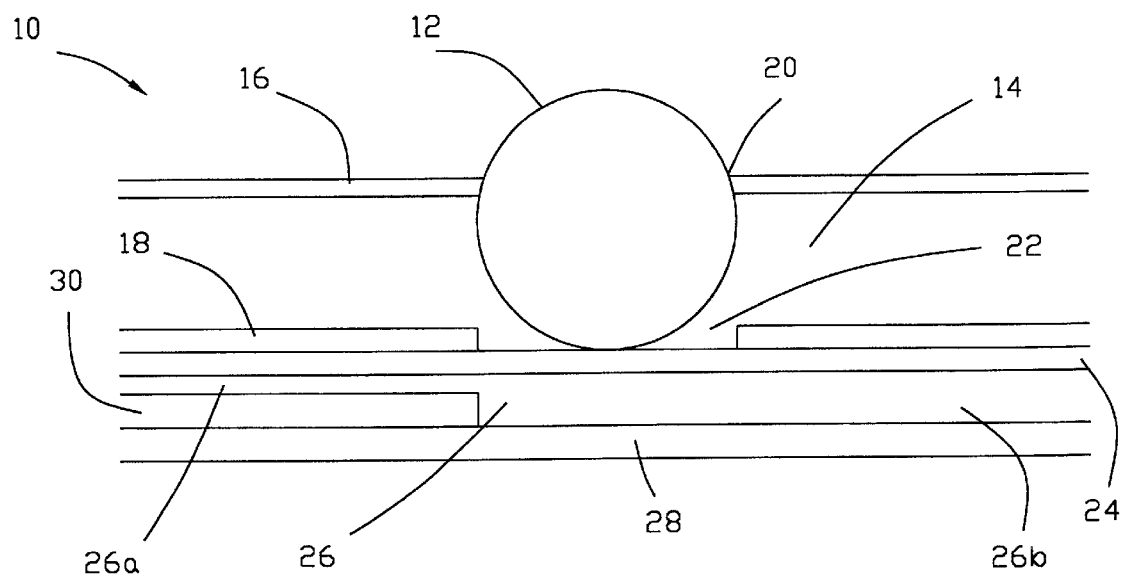
FIG. 1 is a fragmentary cross-sectional view of a microfluidic device containing a basic ball bearing valve according to the present invention.

Referring now to FIG. 1, there is shown a microfluidic valve assembly, generally indicated at 10, which contains a valve constructed according to the present invention. Assembly 10 includes a spherical member or ball bearing 12 which is located within a channel 14 formed between a rigid top layer 16 and a rigid interior layer 18 within assembly 10. Layer 16 and layer 18 each contain a cutout area 20 and 22 respectively within which ball bearing 12 is contained in channel 14. Rigid layers 16, 18 may be constructed from a material such as MYLAR. Spherical member 12 may be constructed from metal, hard plastic, or any other similar material.

A membrane 24 constructed of a flexible material is located adjacent layer 18 opposite channel 14. Membrane 24, which is preferably made from a thin elastomeric material, completely isolates channel 14 from a channel 26 by spanning across cutout area 22. One suitable material that may be used for membrane 24 is polyvinylidene chloride (PVDC) which is the material commonly used as SARAN WRAP(r) film. Channel 26 is capable of carrying fluids within assembly 10, and in the present embodiment is formed by a narrow section 26a and a wider section 26b. Channel section 26b is formed by layer 18 along with adjacent membrane 24, and a rigid bottom layer 28, while section 26a is located between membrane 24 and an additional rigid layer 30 adjacent bottom layer 28.

Figure 2:
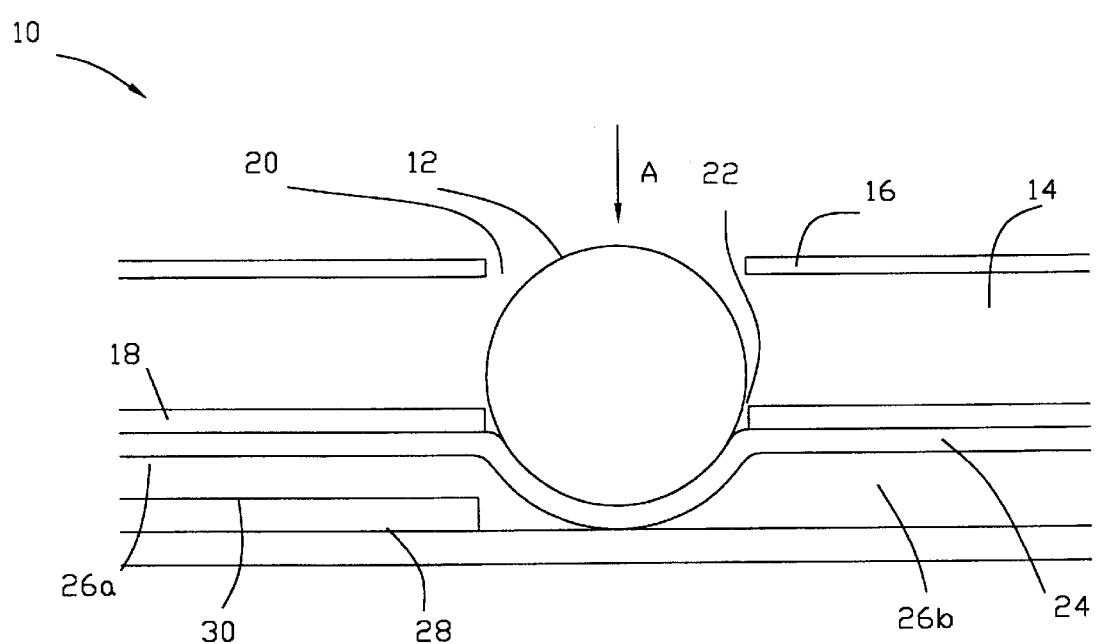
FIG. 2 is a fragmentary cross-sectional view of the valve of FIG. 1 shown in its activated position.

In operation, the flow of a fluid traveling within channel 26 can be controlled within assembly 10 by spherical member 12. Referring now to FIG. 2, member 12 is shifted by a sufficient force in the direction shown by arrow A. This force may be applied manually using the finger of a human operator, or by any suitable mechanical means as known in the art. This movement causes flexible membrane 24 to contact bottom layer 28, closing channel 26 to any fluid movement between channel section 26a and section 26b. Note that layer 18 acts to aid in centering member 12 in the process of activating valve assembly 10, as member 12 is essentially captured within cutout area 22 of layer 18. When the operating force is removed from member 12, said member is shifted back to its unactuated position as shown in FIG. 1 by virtue of the elastomeric property of membrane 24.

Figure 3:
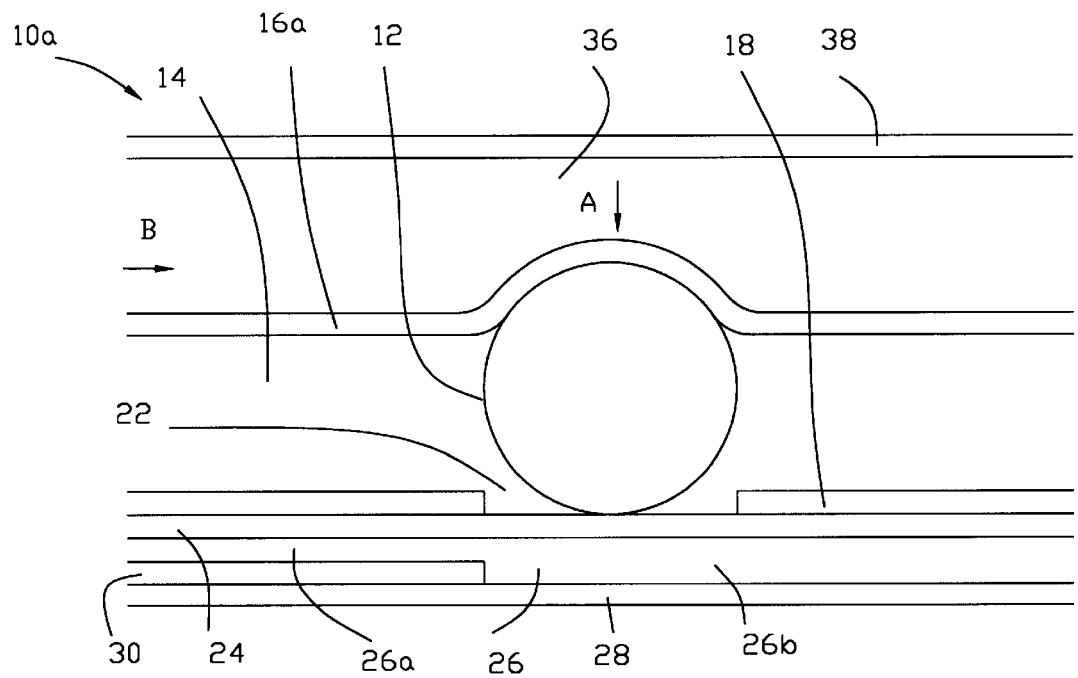
FIG. 3 is a fragmentary cross-sectional view of another embodiment of a ball bearing valve according to the present invention.

FIG. 3 illustrates a second embodiment of a valve assembly constructed according to the present invention. It will be understood that similar parts will be given the same index numerals. Referring now to FIG. 3, there is shown a valve assembly 10a having a spherical member 12 located within a channel 14 which is formed between a layer 18 and an elastomeric layer 16a.

Elastomeric membrane 24 is located adjacent layer 18 opposite channel 14, while spherical member 12 is situated in cutout section 22 within layer 18 and contacts member 24 at this location, as was previously shown in FIG. 1. Channel 26, which consists of a narrow section 26a and a wider section 26b, is formed between membrane 24 and bottom layer 28, and is capable of carrying fluids within a microfluidic circuit.

An upper channel 36 is formed within assembly 10a between layer 16a and a rigid upper layer 38. Channel 36 contains a fluid which is capable of providing a force capable of activating valve assembly 10a. As can be clearly seen in FIG. 3, fluid flowing in the direction of arrow B will flow over spherical member 12, which is located beneath layer 16a.

To operate valve assembly 10a, if the force generated by a fluid flowing in direction B within channel 36, the fluid will force membrane 24 downwardly in the direction of arrow A, causing member 12 to shift and causing membrane 24 to contact layer 28, closing channel 26 to any fluid movement between channel 26a and 26b. When the flow of the fluid within channel 36 is reduced such that the force acting upon member 12 is less than that force exerted by membrane 24 on the lower part of member 12, member 12 will return to the position shown in FIG. 3, and thus allowing fluid flow within channel 26.

Figure 4:
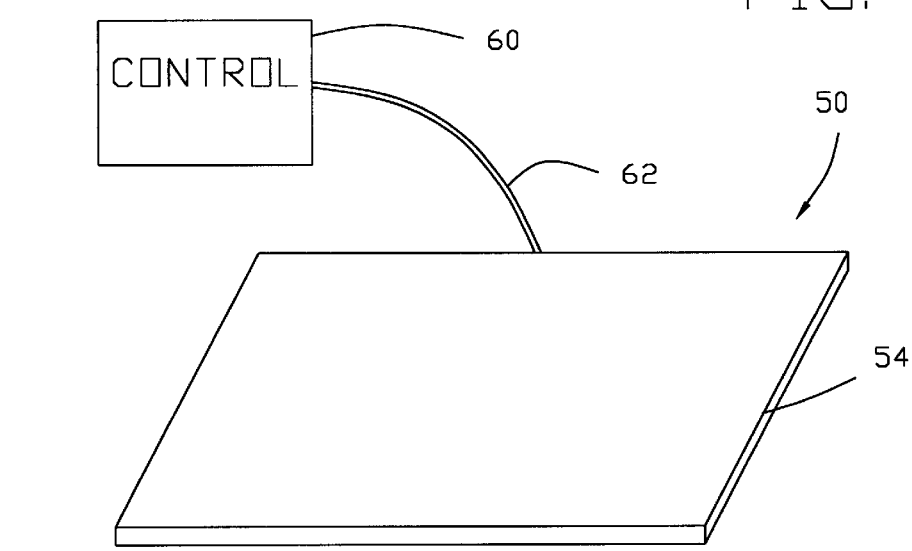
FIG. 4 is a perspective view of a microfluidic array which uses a plurality of ball bearing valves according to the present invention.
Figure 4:
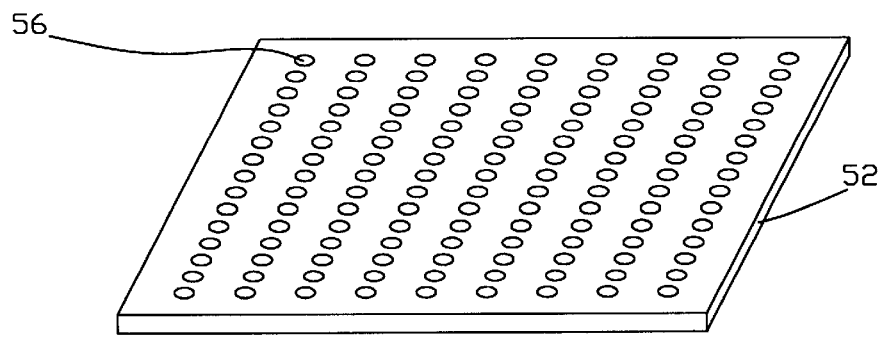

The valve assembly of the present invention can also be used to control a microfluidic array. Referring now to FIG. 4, there is shown a microfluidic array, generally indicated at 50. Array 50 consists of a lower array section 52 and an upper array section 54. Section 52 contains a plurality of spaced apart indentations 56 which are sized to contain a plurality of spherical members 12 as taught in FIGS. 1–3. Also within section 52, there is contained a microfluidic circuit (not shown) which is constructed having channels similar to that shown in FIG. 3. This circuit may be designed to perform many functions which are familiar to those skilled in the art of microfluidic circuitry design.

Section 54 may be constructed similar to the valve circuitry shown in FIG. 3 in that the lower surface is constructed for a elastomeric material which is deformed by spherical members 12 when the valves are in the inactive position. The control of the operation of the valves may be done using fluidic channels, similar to channel 36 in FIG. 3, or operation of the valves may also be accomplished using common electrical, magnetic, or pneumatic means, as is well known in the art.

The control of the operation of array 50 is accomplished by use of external control means 60 which is coupled to section 54 via a cable 62. Control means 60 may be a computer or programmable control or the like, or any device familiar to those skilled in the art. Or, alternatively, array 50 could be inserted as a cartridge into a separate machine which would control operation of the valves within the array.

While the present invention has been shown and described in terms of several preferred embodiments thereof, it will be understood that this invention is not limited to these particular embodiments and that many changes and modifications may be made without departing from the true spirit and scope of the invention as defined in the appended claims.

What is claimed is:

1. A valve for use in a microfluidic structure, comprising:
   a first rigid layer;
   a first flexible layer;
   a first channel, formed between said first rigid layer and said first flexible layer, said first channel having an inlet and an outlet and capable of fluid flow from said inlet to said outlet;
   a spherical actuator located adjacent said first flexible layer on the side opposite said first rigid layer;
   means for shifting said actuator to an actuating position;
   a second rigid layer, located adjacent said first flexible layer on the side opposite said first channel;
   a second flexible layer;
   a second channel, formed between said second rigid layer and said second flexible layer, for containing said spherical actuator;
   a third rigid layer;
   a first aperture, located in said second rigid layer, for positioning said spherical actuator within said second channel during actuation;
   and a third channel, formed between said second flexible layer and said third rigid layer for containing said shifting means;

such that when said actuator is shifted to said actuating position a portion of said first flexible layer is shifted toward said first rigid layer, restricting fluid flow within said first channel.

2. The valve of claim 1, wherein said first flexible layer is constructed from an elastomeric material.

3. The valve of claim 1, wherein said first flexible layer is constructed from polyvinylidene chloride.

4. The valve of claim 1, wherein said spherical actuator comprises a metal ball bearing.

5. The valve of claim 1, wherein said shifting means comprises mechanical operating means.

6. The valve of claim 1, further comprising:
- a second rigid layer, located adjacent said first flexible layer on the side opposite said first channel;
- a second flexible layer;
- a second channel, formed between said second rigid layer and said second flexible layer, for containing said spherical actuator;
- a third rigid layer;
- a first aperture, located in said second rigid layer, for positioning said spherical actuator within said second channel during actuation;
- a third channel, formed between said second flexible layer and said third rigid layer, for containing said shifting means.

7. The valve of claim 1, wherein said shifting means comprises a fluid flowing within said third channel.

8. The valve of claim 1, wherein said second flexible layer comprises an elastomeric material.

9. The valve of claim 1, wherein all of said rigid layers are constructed from MYLAR.

10. A microfluidic control system, comprising:
- a plurality of valves, with each valve comprising
  - a first rigid layer;
  - a first flexible layer;
  - a first channel, formed between said first rigid layer and said first flexible layer, said first channel having an inlet and an outlet and capable of fluid flow from said inlet to said outlet;
  - a spherical actuator located adjacent said first flexible layer on the side opposite said first rigid layer;
  - means for shifting said actuator to an actuating position;
  - a second rigid layer, located adjacent said first flexible layer on the side opposite said first channel;
  - a second flexible layer;
  - a second channel, formed between said second rigid layer and said second flexible layer, for containing said spherical actuator;
  - a third rigid layer;
  - a first aperture, located in said second rigid layer, for positioning said spherical actuator within said second channel during actuation;
  - a third channel, formed between said second flexible layer and said third rigid layer, for containing said shifting means;
  - such that when said actuator is shifted to said actuating position a portion of said first flexible layer in shifted toward said first rigid layer, restricting fluid flow within said first channel;
- and means for controlling the operation of said plurality of valves.

11. The system of claim 10, wherein said controlling means comprises a computer.

12. The system of claim 10, wherein said controlling means comprises a programmable controller.

13. The valve of claim 7, wherein said fluid comprises air.

14. The valve of claim 1, wherein said spherical actuator is constructed from hard plastic.

15. The system of claim 10, wherein all of said rigid layers are constructed from MYLAR.

16. The system of claim 10, wherein said spherical actuators comprises ball bearings.

\* \* \* \* \*